United States Patent [19]

Christenson et al.

[11] 4,329,281

[45] May 11, 1982

[54] HAPTEN COMPOSITIONS

[75] Inventors: James G. Christenson, North Caldwell; Benjamin Pecherer, Montclair, both of N.J.

[73] Assignee: Hoffmann-La Roche Inc., Nutley, N.J.

[21] Appl. No.: 106,347

[22] Filed: Dec. 21, 1979

Related U.S. Application Data

[62] Division of Ser. No. 912,287, Jun. 5, 1978, abandoned.

[51] Int. Cl.³ .............. A61K 39/395; A61K 39/385; C07G 7/00; G01N 33/54
[52] U.S. Cl. ........................... 260/112 B; 23/230 B; 260/112 R; 260/121; 424/8; 424/12; 424/85; 424/88; 424/177
[58] Field of Search ............. 424/8, 12, 85, 88, 177; 260/112 R, 112 B, 121; 23/230 B

[56] References Cited

U.S. PATENT DOCUMENTS

| | | |
|---|---|---|
| 3,352,901 | 11/1967 | Schultz . |
| 3,690,834 | 9/1972 | Goldstein .......................... 23/230 R |
| 3,996,344 | 12/1976 | Gross ..................................... 424/1.5 |
| 4,016,146 | 4/1977 | Soares .............................. 260/112 R |
| 4,041,076 | 8/1977 | Avenia ............................. 260/559 A |

FOREIGN PATENT DOCUMENTS 2517229  10/1976  Fed. Rep. of Germany ........ 424/12

*Primary Examiner*—Anna P. Fagelson
*Attorney, Agent, or Firm*—Jon S. Saxe; Bernard S. Leon; James H. Callwood

[57] ABSTRACT

Novel hapten compositions consisting of 4-[4-[2-(aminopropyl)]phenyl]butanoic acid and its N-methyl derivative are useful in preparing immunogens which can be respectively employed in the elicitation of antibodies selective to amphetamine and methamphetamine. These antibodies can be used as reagents in immunoassays for these two compounds.

3 Claims, No Drawings

HAPTEN COMPOSITIONS

This is a division of application Ser. No. 912,287, filed June 5, 1978, now abandoned.

BACKGROUND OF THE INVENTION

U.S. Pat. No. 3,996,344 and 4,016,146 disclose the preparation of haptenic compounds which are useful in preparing immunogens which can elicit amphetamine specific antibodies on immunization of a host animal. The haptenic compounds disclosed have the general structure:

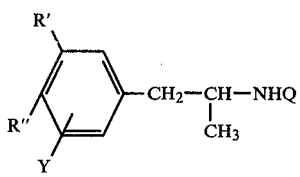

where R' and R'' each, inter alia, independently can be hydrogen, Q can be hydrogen or methyl and Y, inter alia, can be

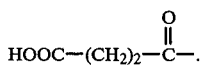

While the above general structure allows for the construction of a hapten corresponding to methamphetamine when R' and R'' are both hydrogen and Q is methyl, the specification of the reference patent suggests only the Q is methyl when at least one of R' and R'' are other than hydrogen.

The antibodies produced from immunogens incorporating the aforesaid haptenic compounds are indicated to be useful in immunoassays for detecting the target compound, such as amphetamine, in biological fluids.

U.S. Pat. No. 4,041,076 discloses haptenic compounds useful in preparing immunogens which can elicit antibodies selective to the amphetamines which haptenic compounds have the general structure:

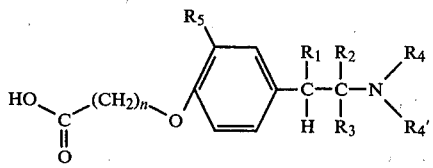

where, inter alia, n can be 3, $R_1$ and $R_2$ can be hydrogen, $R_3$ can be lower alkyl including methyl, $R_4$ can be hydrogen or lower alkyl including methyl and $R'_4$ can be hydrogen.

See also U.S. Pat. No. 3,878,187 for a disclosure relating to the same type of haptenic compounds as immediately above.

U.S. Pat. No. 3,690,834 teaches the preparation of antigens and antibodies to a large number of biologically active compounds. The antigens are prepared by linking the compounds to a protein carrier through a suitable linkage. These antigens may then be used to elicit antibodies by conventional procedures. The antibodies and spin labelled derivatives of the biologically active compounds are then used in an assay procedure. One of the class of active compounds disclosed to the amphetamine (column 9, line 54 to column 10, line 4).

DESCRIPTION OF THE INVENTION

The present invention relates to novel haptenic compounds of the formula

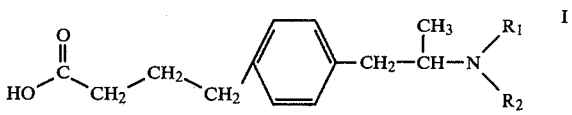

where $R_1$ is hydrogen or methyl and $R_2$ is hydrogen or a conventional amine protecting group.

The N-protected form of the haptenic compounds of formula I is employed to prevent self-condensation reactions during further transformations in the preparation of the corresponding immunogen. Such protective groups can be readily cleaved by procedures well known in the art to yield the corresponding immunogen wherein $R_2$ is hydrogen. A preferred amine protecting group is t-butyloxycarbonyl (t-Boc).

In order to prepare the immunogens needed in the present invention, it is necessary that the hapten of formula I be covalently bonded through the carboxylic group to a conventional immunogenic carrier material. As used herein, the term "immunogenic carrier material" is meant to include those materials which have the property of independently eliciting an immunogenic response in a host animal and which can be covalently coupled to the above described haptens. Suitable carrier materials include, for example: proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an immunogen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. Other suitable protein products will be suggested to one skilled in art. It is generally preferred but not necessary that proteins be utilized which are foreign to the animal hosts in which the resulting antigen will be employed.

The covalent coupling of the hapten to the immunogen carrier material can be carried out in a manner well known in the art for establishing amide bonds. However, to ensure an adequate degree of coupling under the mildest possible conditions so as to minimize any possible deleterious effect on the carrier material it may be desirable to convert the hapten of formula I to an isolatable activated form prior to coupling. One particularly preferred isolatable activated form is the N-hydroxysuccinimide ester as indicated by formula II.

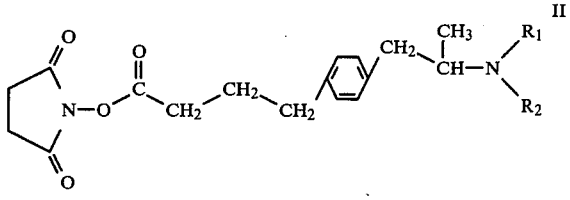

wherein $R_1$ and $R_2$ are as above.

Other suitable isolatable activated derivatives include the p-nitrophenyl esters; acylimidazoles; and so forth. Other methods for coupling may be employed wherein the activated intermediates need not be isolated. Such methods include the mixed anhydride method, use of EEDQ (N-ethoxycarbonyl-2-ethoxy-1,2-dihydroquinoline) as coupling agent and the like.

The coupling of the hapten either as the free acid of formula I or more preferably as an activated derivative, e.g., formula II to the immunogenic carrier material can be readily accomplished utilizing techniques now well known in the art for establishing amide bonds. Thus, for example, one such technique would involve dissolving the carrier material and a coupling agent in a suitable inert solvent followed by adding the desired hapten of formula II. The reaction may be conducted in a temperature in the range of from about 0° C. to about 50° C. although higher or lower temperatures might be employed depending on the nature of the reactants. A most preferable temperature is about room temperature.

The coupling agent which may be used in the aforesaid reaction will be selected from those commonly employed in organic chemistry for initiating amide bond formation. A particularly suitable group of coupling agents comprise the carbodiimides, most preferably dicyclohexylcarbodiimide or 1-ethyl-3-(3- dimethylaminopropyl)carbodiimide. The molar ratio of the hapten to the carrier material will, of course, depend on the identity of the hapten utilized and the protein selected for the reaction.

Conventional conditions for the coupling reaction can be employed. Thus when utilizing carbodiimides as coupling agents, it is desirable to utilize a slightly acidic reaction medium for this step, e.g., a medium having a pH in the range of from about 3 to 6.5, most preferably in the range of from about 4 to 6.5. Upon completion of the reaction, the excess hapten molecules may be removed by dialysis.

As indicated previously, one preferred technique for preparing the immunogen of the present invention is to first prepare and isolate an activated derivative, i.e., a compound of formula II, and then to react this compound with the carrier material to form the blocked antigen. Such activated derivatives are conveniently prepared by reacting a compound of formula I with a desired activating compound, such as N-hydroxysuccinimide, and a coupling agent, such as dicyclohexylcarbodiimide, in an inert solvent. The reaction is usually allowed to proceed for 16-60 hours at reduced temperature (0°-5° C.). The activated derivative may then be isolated by filtering off the by-product, dicyclohexylurea, and distilling the solvent.

The hapten may then be coupled to the carrier material by contacting the activated derivative with the chosen carrier material. When the activated derivative is the N-hydroxysuccinimide ester and the carrier material is bovine serum albumin, this may be accomplished by adding the activated derivative in a water-miscible solvent to an aqueous solution of the carrier material containing a base, such as sodium bicarbonate.

Another method of coupling carrier protein to hapten (formula I) is by activating the carboxyl group of the hapten without isolation of an intermediate and adding the activated hapten to the carrier protein. An example of such a reaction is the mixed anhydride obtained by reaction with isobutylchloroformate. The hapten is dissolved in an anhydrous, water-miscible organic solvent, usually dioxane, and the solution is neutralized with an equimolar quantity of triethylamine. After stirring at room temperature the temperature of the mixture is reduced to between 9° and 8° C. An equimolar quantity plus 10% excess of isobutylchloroformate is then added and stirring is continued. Meanwhile, the carrier protein, e.g., bovine serum albumin, is dissolved in water and the pH is adjusted to 9.0 with NaOH. The quantity of carrier used is equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight. The final ratio or organic solvent to water is 1:1.

The mixture is then adjusted to neutrality, the aqueous-organic solvent is removed and aqueous solution is effected. After dialysis and lyophilization, the amine-protecting group is removed.

Following coupling of a compound of either formula I or formula II to the carrier material, it is necessary to remove the protective group ($R_2$ in formulas I and II), in order to restore the free primary or secondary amino function. In the case of the t-butoxycarbonyl protective group, this may be conveniently achieved by treating the material with trifluoroacetic acid in dichloromethane at room temperature. The relative amounts of trifluoroacetic acid and dichloromethane and the time duration of the treatment may be varied to suit particular cases. In general, from one to three volumes of dichloromethane per volume of trifluoroacetic acid and reaction times of 30 to 60 minutes have been found to give good results.

The antigens of the present invention may be utilized to induce formation of antibodies in host animals by injecting the immunogen in such a host, preferably using an adjuvant. Improved titers can be obtained by repeated injections over a period of time. Suitable host animals for this purpose include mammals such as rabbits, horses, goats, guinea pigs, rats, cows, sheep etc. The resulting antisera will contain antibodies which will selectively complex with amphetamine if in the immunogen $R_1$ is hydrogen or methamphetamine if $R_1$ is methyl.

The specific antibodies of the present invention are useful as reagents for the determination of the amphetamines. In such an assay, a known amount of labelled amphetamine or methamphetamine is mixed with the above antibody and a sample containing some amphetamine or methamphetamine added. The amount of amphetamine or methamphetamine in the sample can be determined by measuring the inhibition of the binding to the specific antibody of the labelled amphetamine or methamphetamine by the unknown sample in comparison to known standard solutions of the compound to be determined. The reagents may be added in any order. A suitable assay procedure for this purpose is described in greater detail in U.S. Pat. No. 3,709,868.

Suitable labelled amphetamine or methamphetamine for assay purposes include radioisotopically labelled amphetamine or methamphetamine or derivatives thereof particularly those labelled with tritium ($^3$H), carbon 14 ($^{14}$C) or with iodine 125 ($^{125}$I). One may also employ amphetamine or methamphetamine labelled with any other unique and detectable label such as for example an electron spin resonance group. Examples of the use of various electron spin resonance labelled molecules in bioassays are to be found U.S. Pat. Nos. 3,453,288, 3,481,952 and 3,507,876. Other suitable labels include chromophores, fluorophors, enzymes, red blood cells, latex particles, etc.

It is also within the skill of the art to employ labelled antibody in the aforesaid procedure as the tracer compound.

The preparation of haptenic compounds of formula I can readily be accomplished from amphetamine ($R_1$=hydrogen) or methamphetamine ($R_1$=methyl).

In the initial step of this procedure the starting compound is treated with an acylating agent in conventional manner so as to form the corresponding N-acyl derivative. A preferred N-acyl derivative is the acetyl derivative. Another useful derivative for the purpose of the instant procedure is the trifluoroacetyl derivative which is obtained by reacting the starting compound with trifluoroacetic anhydride.

In the next step of the procedure the N-acyl derivative is reacted with succinic anhydride in the presence of aluminum chloride under conventional Friedel-Crafts conditions so as to produce a compound of the formula

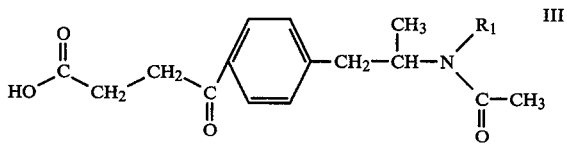

where $R_1$ is as above.

The compound of formula III is then subjected to catalytic hydrogenation in a manner known per se to reduce the keto function to a methylene group. A preferred catalyst for this procedure is palladium on charcoal. There is thus produced a compound of the formula

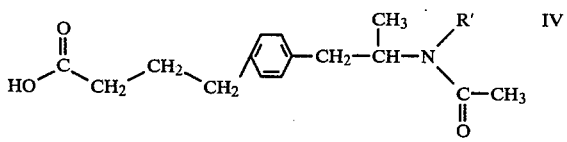

where $R_1$ is as above.

The desired haptenic compounds of the present invention can be obtained by base or acid hydrolysis of the acetyl group.

The instant invention is further illustrated by reference to the following Examples. All temperatures are in degrees centigrade unless otherwise indicated.

EXAMPLE 1 rac.N-(alpha-Methylphenethyl)acetamide

Seventy three and six tenths g (0.2 moles) of rac. amphetamine sulfate was suspended in 150 ml of water and to the stirred suspension, a solution of twenty g (0.5 moles) of sodium hydroxide in 200 ml of water was added. The liberated oil was collected by three extractions with 200-ml portions of toluene. The combined extracts were dried over anhydrous $K_2CO_3$, then the drying agent removed by filtration. To the filtrate, 100 ml of acetic anhydride (1.0 mole) was added in portions and the resulting solution refluxed for two hours. The toluene, excess anhydride and acetic acid were distilled in the rotary evaporator and the residual oil distilled in a simple Claisen still collecting the fractions that boiled at 120°–126°/7 mm, yield 63.3 g (89%) of a colorless oil that spontaneously set to a mass of crystals, mp 91°–93°.

TLC on silica gel G using System A:ether-ethanol ammonium hydroxide (90:10:2, v/v/v) as developer showed the material was homogeneous.

EXAMPLE 2 rac.4-[4-[2-(Acetylamino)propyl]phenyl]-4-oxobutanoic acid

In a one l., three necked, creased flask provided with a stirrer, thermometer, condenser topped with a drying tube and a short length of Gooch tubing connected to a small Erlenmeyer flask was placed 18.7 g (0.106 moles) of N-(alpha-methylphenethyl) acetamide, 15.9 g (0.159 moles) of succinic anhydride and 500 ml of dry methylene chloride. The flask and contents were cooled to 0°–5°, and from the Erlenmeyer flask through the Gooch tubing, 55.5 g (0.424 moles) of anhydrous aluminum chloride was added in small portions over a period of approximately 0.5 hour. A sharp exotherm occurred after each of the first additions, but the temperature was not allowed to exceed 8°. During the addition, the succinic anhydride slowly dissolved and gradually a grayish green gum was deposited. After five hours at 0°–5°, the cooling bath was removed, and the stirred mixture allowed to warm to room temperature (19°–22°), then stirred for another twenty-four hours. At the end of this time, the reaction mixture consisted of a reddish orange gum and a pale-colored solvent. The mixture was cooled in an ice bath, and with vigorous stirring 200 ml of 3 N hydrochloric acid added at 20°. The mixture was stirred until the color of the viscous red gum became grayish white. The stirrer was then stopped, the layers allowed to separate, and the lower methylene chloride layer removed by suction from the reaction vessel. Another 300 ml of methylene chloride was added to the flask, the contents stirred for five minutes, then allowed to settle and the lower layer drawn off as before.

The combined methylene chloride layers were washed once with 200 ml of water and the water wash added to the aqueous layer in the reaction flask. The contents of the reaction vessel were stirred for eighteen hours during which time the gum was converted to a crystalline white solid. This solid was recovered by filtration, washed with water, then dried in vacuo at 80°; yield 23.34 g (79%) of practically pure material, mp 142°–145°. Recrystallization of this product from 250 ml of acetonitrile (charcoal) gave 22.3 g (75%) of a white crystalline solid, m.p. 143.5°–146°.

Microanalysis: C, 64.95; H, 6.90; N, 5.17 Calcd for $C_{15}H_{19}NO_4$: C, 64.97; H, 6.91; N, 5.05. TLC (System A) showed the product was uniform.

EXAMPLE 3 rac.4-[4-[2-(Acetylamino)propyl]phenyl]butanoic acid

Four and two-tenths g (0.015 moles) of 4-[4-[2-(Acetylamino)propyl]phenyl]-4-oxobutanoic acid was shaken under fifty lb/in$^2$ of hydrogen pressure in 200 ml of acetic acid in the presence of one gram of 10% Pd/C in a Parr apparatus. Reduction was complete in approximately 1.25 hours. After removal of the catalyst by filtration, the solvent was distilled in the rotary evaporator leaving 3.8 g of a colorless syrup. An aliquot of the syrup was rubbed under acetonitrile whereupon it crystallized. Recrystallization from acetonitrile yielded white crystals of mp 114°–117°.

Microanalysis: C, 68.21; H, 8.04; N, 5.36. Calcd. for $C_{15}H_{21}NO_3$: C, 68.42; H, 8.04; N, 5.32. TLC (System A) showed that the reduction was complete.

EXAMPLE 4 rac.4-[4-[2-(Amino)propyl]phenyl]butanoic acid hydrochloride

Basic Hydrolysis:

The residual syrup from Example 3 was refluxed with 3 g (0.075 moles) of sodium hydroxide in 50 ml of water for 30.5 hours, then the resulting solution cooled, and acidified to pH 7 by the addition of hydrochloric acid, whereupon a precipitate of silica separated. After filtration hydrochloric acid was added to the filtrate to pH 3 and the solution distilled to dryness. The residual solid was dissolved in a small volume of hot water, the solution filtered to remove a small amount of silica, and on chilling, long needle-like crystals separated, yield one g, mp 200°–202.5°. A second crop of two g was recovered by concentrating the mother liquor and chilling, mp 198°–200°.

The combined solids were dissolved in a small amount of hot acetic acid, a trace of insoluble material removed by filtration, and ethyl acetate added to the hot filtrate to the cloud point. After chilling for two hours, the crystals that separated were recovered and dried, mp 200°–203°.

Microanalysis: C, 60.78; H, 7.86; N, 5.44; Cl, 13.73. Calcd for $C_{13}H_{19}NO_2\cdot HCl$: C, 60.58; H, 7.82; N, 5.43; Cl, 13.75.

Acidic Hydrolysis:

The partially crystalline residue obtained from the hydrogenation of 25.9 g (0.0935 moles) of the residue from Example 3 was refluxed with 250 ml of 20% hydrochloric acid for 6.5 hours. The cooled solution was transferred to a separatory funnel and shaken three times with 75 ml portions of methylene chloride, then the aqueous layer was distilled in the rotary evaporator to a syrup that partially crystallized. After storing this residue overnight in a dessicator with calcium chloride and sodium hydroxide at 0.3 mm, complete solidification occurred, wt. 26 g. The solid was dissolved in a hot mixture of 100 ml each of acetic acid and ethyl acetate, a small amount of insoluble material was removed by filtration and the warm filtrate diluted with 200 ml of ethyl acetate. After crystallization had started, the mixture was chilled for two hours in an ice bath. Yield 8.51 g of mp 198°–200°. A second crop of 4.1 g, mp 195°–198° was obtained from the mother liquor.

TLC of the solid obtained by distillation of the solvent from the mother liquor showed that little, if any, amino acid hydrochloride was present, but that it consisted mainly of the unhydrolyzed acetyl compound. No attempt was made to recover any further material from this residue.

EXAMPLE 5 rac.4-[4-[2[[(t-Butyloxy)carbonyl]amino]propyl]phenyl]butanoic acid

Eight and seventy-five hundredths g (0.03 moles) of rac. 4-[4-[2-(amino)propyl]phenyl]butanoic acid hydrochloride and 2.4 g of magnesium oxide (0.06 moles) were stirred together in 75 ml of water for ten minutes, then 8.6 g (0.06 moles) of freshly distilled t-butyl azidoformate in 75 ml of dioxane was added, and the suspension stirred for twenty-six hours at 40°–45°. The dioxane was distilled in the rotary evaporator and to the pasty residue 150 ml of water was added, followed by dropwise addition of acetic acid to pH 4. The partially solidified mixture was extracted with three 50-ml portions of methylene chloride, the turbid, combined methylene chloride extracts washed with a little water, then dried and distilled in the rotary evaporator. The remaining syrup was dissolved in fifty ml of toluene and 100 ml of Skelly B, the solution filtered, and another fifty ml of Skelly B added to the cloud point. On seeding, crystallization began and was completed by chilling at 8° overnight. The crystalline product was recovered by filtration, washed with a little hexane, and dried. Yield 7.96 g of mp 91.5°–93.5°.

An analytical sample was obtained by recrystallization of an aliquot from ethyl acetate-Skelly B after which the product melted at 93.5°–95.0°.

Microanalysis: C, 67.46; H, 8.42; N, 4.29. Calcd. for $C_{18}H_{27}NO_4$: C, 67.27; H, 8.47; N, 4.36.

EXAMPLE 6

N-Hydroxysuccinimide ester of rac.4-[4-[4-[2-[[(t-butoxy)carbonyl]amino]propyl]phenyl]butanoic acid Three and two tenths g (0.01 mole) of rac.4-[4-[2-[[(t-butyloxy)carbonyl]amino]propyl]phenyl]butanoic acid and 1.45 g (0.0126 moles) of N-hydroxysuccinimide were dissolved in forty ml of 1,2-dimethoxyethane and to the solution 2.56 g (0.0125 moles) of dicyclohexylcarbodiimide was added. Within a few minutes crystals of dicyclohexylurea began to separate. The mixture was then stored at 5° for forty-eight hours. The insoluble dicyclohexylurea was removed by filtration and the solvent distilled in the rotary evaporator at 40°, leaving 5.26 g of syrup. The syrup was dissolved in sixty ml of ethyl acetate and the resulting solution maintained at room temperature for an hour or so during which time a further 0.2 g of dicyclohexylurea separated; this was removed by filtration. After distillation of the solvent in the rotary evaporator, the residual syrup was dissolved in fifty ml of ethyl acetate and sufficient Skelly B added to incipient turbidity. Crystallization was initiated by seeding and completed by chilling at 5° for 18 hours. Yield 1.99 g of mp 88.5°–90°. A second crop of 0.65 g, mp 81°–84° was obtained by concentrating the filtrate and chilling. Both crops of material analyzed correctly and had identical nmr spectra.

Microanalysis: C, 63.21; H, 7.33; N, 6.82. Calcd. for $C_{22}H_{30}N_2O_6$: C, 63.19; H, 7.23; N, 6.69.

EXAMPLE 7 rac.N-(N,alpha-Dimethylphenethyl)acetamide

A total of 140 g of methamphetamine was refluxed in 1.2 l. of toluene together with 250 ml of acetic anhydride for 1.25 hr. After removal of the solvent, acetic acid and excess anhydride, the residual oil was distilled through a 4" Vigreux column mounted on a Claisen head; the following fractions were collected:

| Fraction 1 | bp 56–100°/0.25mm | 12.5g $n_D^{23}$ 1.5050 |
|---|---|---|
| Fraction 2 | bp 100–105°/0.25mm | 10.5g $n_D^{23}$ 1.5188 |
| Fraction 3 | bp 105–106°/0.25mm | 145.9g $n_D^{23}$ 1.5219 |
| Residue | | 3.0g dark oil |

Fraction 3 was taken as pure product, yield 76% based on phenylacetone.

Microanalysis: C, 75.38; H, 8.98; N, 7.39. Calc for $C_{12}H_{17}NO$: C, 75.34; H, 8.96; N, 7.32.

EXAMPLE 8 rac.4-[4-[2-(Acetylmethylamino)propyl]phenyl]-4-oxobutanoic acid

To seventy-six and four tenths g (0.4 mole) of N-(N,alpha-dimethylphenethyl) acetamide and 60.4 g (0.6 mole) of succinic anhydride in 2l. of dry methylene chloride at −15° to −10°, 213 g (0.8 mole) of anhydrous chloride was added over a period of one hour. A gummy brown solid gradually formed, as the color of the reaction mixture became yellow-green. The mixture was stirred for 64 hours at ice temperature, and then hydrolyzed by the dropwise addition of 400 ml of 6 N hydrochloric acid at T<10°. As the hydrolysis proceeded a cloudy white precipitate formed and stirring was continued until all of the brown lumps had disappeared. The stirrer was stopped whereupon the curdy solids adhered to the walls of the flask and a clear methylene chloride layer separated. This was decanted from the solid and the process repeated by stirring the solid for thirty minutes with another one-l. portion of methylene chloride.

To the residual solid, 500 ml of water was added and a slow stream of nitrogen passed over the vigorously-stirred suspension whereupon the gummy solid was converted to a finely divided granular gray solid as the methylene chloride was swept from the flask. After the transformation was complete (0.5–1 hr) the grayish solid was recovered by filtration and washed with water. The damp filter cake was suspended in one liter of water and concentrated ammonium hydroxide added dropwise to a pH of 9–10; the bulk of the solids dissolved leaving a small insoluble residue of aluminum hydroxide. After heating on the steam bath for 0.5 hr, the insoluble material was removed by filtration through a bed of filteraid and the acid reprecipitated by the dropwise addition of hydrochloric acid to pH 3. The almost-white acid was recovered by filtration, washed, and dried for 18 hr at 65° in the vacuum oven; yield 74.7 g (64%), mp. 144°–147°. This material was analytically pure.

Microanalysis: C, 65.90; H, 7.13; N, 4.92. Calc. for $C_{16}H_{21}NO_4$: C, 65.96; H, 7.27; N, 4.81.

EXAMPLE 9 rac.4-[4-[2-(Acetylmethylamino)propyl]phenyl]-butanoic acid

The catalytic reduction of the oxo-acid of Example 8 was carried out in the same manner as described in Example 3; the catalyst-substrate ratio was decreased to 1.5 g/0.05 mole using the 200 ml of acetic acid as solvent. Quantitative yields were obtained. After recrystallization of an aliquot from acetonitrile, the mp was 116.5°–120°.

Microanalysis: C, 69.27; H, 8.11; N, 5.16. Calc for $C_{16}H_{23}NO_3$: C, 69.29; H, 8.36; N, 5.05.

EXAMPLE 10 rac.4-[4-[2-(methylamino)propyl]phenyl]butanoic acid

The crude product obtained by the hydrogenation of 29.2 g (0.1 mole) of the oxoacid in Example 9 was suspended in 100 ml of water, 10% sodium hydroxide was added to pH 9, followed by 16 g of sodium hydroxide and the solution refluxed for 48 hours. To the warm solution, sufficient hydrochloric acid was added to bring the pH to 3, which produced a copious precipitate of silica. This suspension was refluxed for 2.5 hr to coagulate the silica which was removed by filtration on a bed of filteraid. Attempts to crystallize the hydrochloride or the zwitterion (at pH 7) were futile, therefore the solution was passed over a column of 550 ml of Dowex (H) (40×290 mm). The column was washed with about one liter of distilled water until the pH was 6, then the amino acid eluted with 1.5 liter of 10% pyridine in water; the acid was recovered in the last 750 ml of effluent (pH 6–9). Distillation of this solution in the rotary evaporator followed by repeated distillation after the addition of water to the syrupy residue yielded a solid residue. This solid was dissolved in 125 ml of hot ethanol, a trace of insoluble material removed by filtration, and 250 ml of ethyl acetate added to the filtrate. After 18 hr at room temperature, the crystals that had separated were recovered, they were washed with a little ethyl acetate containing a small amount of alcohol and dried. There was obtained 11.2 g (47%) of white crystalline material, mp 169.5°–172°.

Microanalysis: C, 71.32; H, 9.16; N, 5.96. Calc for $C_{14}H_{21}NO_2$: C, 71.46; H, 8.99; N, 5.96.

EXAMPLE 11 rac.4-[4-[2-[(t-Butoxycarbonyl)methylamino]propyl]phenyl]butanoic acid

This material was prepared by exactly the same method as that used for the norcompound in Example 5. From 11.8 g (0.05 moles) of rac. 4-[4-[2-(methylamino)propyl]phenyl]butanoic acid, 8.50 g of the t-BOC derivative of mp 75.5°–77.5° was obtained (50%).

Microanalysis: C, 67.88; H, 8.57; N, 4.09. Calc for $C_{19}H_{29}NO_4$: C, 68.03; H, 8.71; N, 4.18.

EXAMPLE 12 rac.4-[4-[2-[(Trifluoroacetyl)methylamino]propyl]phenyl]butanoic acid

Fifteen g. of trifluoroacetic anhydride containing 2.53 g (0.01 mole) of the amino acid, of Example 10 was refluxed for 4.5 hr. The excess anhydride and acid were removed in the rotary evaporator, the residual oil taken up in chloroform, washed with water, dried and the solvent distilled. A non-crystallizing oil was obtained.

An aliquot of this oil was distilled in the Kugelrohr apparatus and the fraction boiling at 180°–190°/0.1 mm collected. This oil failed to crystalize Microanalysis: C, 57.72; H, 6.19; N, 4.26. Calc for $C_{16}H_{20}F_3NO_3$: C, 58.00; H, 6.08; N, 4.23.

A crystalline S-benzylisothiuronium salt was prepared from the above substance in the usual manner. After recrystallization from water, the salt melted at 139.5°–141°.

EXAMPLE 13 rac.4-[4-[2-[(t-Butoxycarbonyl)methylamino]propyl]-phenyl]butanoic acid N-hydroxysuccinimide ester A total of 3.35 g (0.01 moles) of the protected acid of Example 11 was dissolved in 60 ml of ethylene glycol dimethyl ether and to this solution 1.45 g of N-hydroxy succinimide (0.126 moles) was added, followed by 2.56 g of dicyclohexylcarbodiimide (0.0125 moles). As soon as the solution was complete, the flask was placed in an ice bath and kept there for 22 hr. The suspension was allowed to warm to room temperature and 2.50 g of dicyclohexylurea was recovered by filtration. The solvent was distilled from the filtrate leaving a semi-solid residue that was dissolved in 125 ml of ethyl acetate. To this solution, ten drops of acetic acid was added, and the solution allowed to stand for 0.5 hr. From this another 0.44 g of dicyclohexylurea was recovered. Removal of the solvent left 5.29 g of a colorless oil, that was dissolved in 50 ml of ethanol and refrigerated at 5° for 18 hr. A small crop of crystalline material mp 140.5°–143° was removed by filtration. After distillation of the alcohol, the material was redissolved in 50 ml of ethyl acetate and another small quantity of the same crystalline material separated. Removal of the solvent left a pale-colored oil that was maintained at 0.2 mm at 40° for 18 hr; it weighed 4.51 g. The uv analysis of this material indicated a purity of 88–89%.

EXAMPLE 14

Preparation of Immunogen

Bovine serum albumin (BSA) (300 mg) was dissolved in 12 ml of water and 6 ml of 0.5 M sodium bicarbonate was added. The N-hydroxysuccinimide ester (63 mg) was dissolved in 6 ml of dimethoxyethane and added dropwise to the BSA solution with stirring. The solution was stirred for 4 hours at room temperature, then allowed to stand at 4° overnight. The solution was then diluted to approximately 50 ml. with water and concentrated by ultrafiltration (Amicon PM-10 membrane) to 5–10 ml. This dilution and concentration procedure was carried out at least four times or until the $A_{260}$ of the filtrate had decreased from approximately 25 to less than 0.2. The final concentrate was dialyzed overnight at 4° against 1 liter of water. The dialysate was changed and dialysis repeated twice for about 4 hours each time. The solution was then lyophilized. The lyophilized material was redissolved in 10 ml of trifluoroacetic acid/dichloromethane (1/1, v/v) and allowed to stand for at least 30 min. in the dark at room temperature.

The solution was then evaporated to dryness under a stream of nitrogen. The residue was resuspended in 20 ml of water and brought to pH 6–9 with 1 N sodium hydroxide. The resulting clear, colorless solution was dialyzed against one liter of phosphate buffered saline (0.9% NaCl in 0.005 M sodium phosphate, pH 7.2) overnight at 4°. The dialysate was changed and dialysis continued for 4 hr. By following the above procedures with the products of Example 6 and Example 13 immunogens are obtained useful in eliciting antibodies selective for amphetamine and methamphetamine respectively.

EXAMPLE 15

Immunization and Bleeding

The immunogen of Example 14 useful in eliciting antibodies to amphetamine was diluted with phosphate buffered saline to an $A_{274}$ of approximately 1.0. The diluted immunogen was then emulsified with an equal volume of Freund's adjuvant. The resulting material was used to inoculate five rabbits. Each innoculation comprised two subcutaneous injections of 0.5 ml of each.

Test bleedings obtained 25 days after initiation of immunization, four weekly injections given, showed a significant ability to bind $^{125}$I-labelled rac. 4-hydroxy-alphamethylphenethylamine ($^{125}$I-amphetamine analog—see U.S. Pat. No. 4,041,076) as seen in Table I below:

TABLE I

| | Binding of $^{125}$I-amphetamine antigen by rabbit sera | |
|---|---|---|
| Rabbit No. | $^{125}$I in supernatant (cpm/0.5 ml) | Binding (%) |
| 20 | 12759 | 26 |
| 21 | 6963 | 60 |
| 22 | 7110 | 59 |
| 23 | 7762 | 55 |
| 24 | 8131 | 53 |
| Normal Serum | 17201 | — |

Test bleedings obtained after 48 days, seven weekly injections, showed an increased ability to bind the $^{125}$I-antigen as seen in Table II.

TABLE II

| | Binding of $^{125}$I-amphetamine antigen by rabbit sera | |
|---|---|---|
| Rabbit No. | $^{125}$I in supernatant (cpm/0.5 ml) | Binding (%) |
| 20 | 1324 | 90 |
| 21 | 776 | 94 |
| 22 | 846 | 93 |
| 23 | 1121 | 91 |
| 24 | 1212 | 90 |
| Normal Serum | 12730 | — |

The above sera were diluted to the highest dilution yielding approximately 75% binding of the $^{125}$I-antigen and the results are summarized in Table III.

TABLE III

| | Titration of rabbit sera | |
|---|---|---|
| Rabbit No. | Dilution | Binding |
| 20 | 1:20 | 75% |
| 21 | 1:120 | 82% |
| 22 | 1:120 | 80% |
| 23 | 1:30 | 79% |
| 24 | 1:30 | 75% |

The cross reactivity of a number of potential cross-reactants were determined for each serum at the appropriate dilution and the results are set forth in Table IV.

TABLE IV

Reactivity of five potential cross-reactants in RIA using rabbit sera

| Compound | Conc'n. (ng/ml) | Rabbit No.: 20 | 21 | 22 | 23 | 24 |
|---|---|---|---|---|---|---|
| | | Dilution: 1:20 | 1:120 | 1:120 | 1:30 | 1:30 |
| | | Amphetamine equivalents (ng/ml) | | | | |
| Phenmetrazine | 10,000 | 145 | 133 | 305 | 227 | 0 |
| Phentermine | 10,000 | 188 | 190 | 558 | 283 | 106 |
| Phenyl-propanol-amine . HCl | 10,000 | 185 | 200 | 713 | 341 | 301 |
| Propyl-hexedrine | 10,000 | 3 | 3 | 3 | 8 | 3 |
| Tyramine | 10,000 | 93 | 22 | 92 | 76 | 32 |

These data demonstrate the feasibility of a radioimmunoassay based on the use of the present immunogen. A suitable assay procedure is given in U.S. Pat. No. 4,041,076.

We claim:

1. An antibody specific to amphetamine prepared by inoculating a host animal with an immunogen of the formula

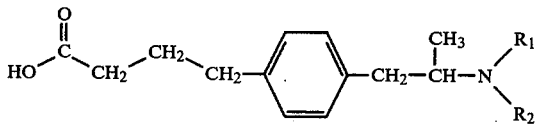

which is covalently bonded through the carboxyl group to an immunogenic carrier material, where $R_1$ is hydrogen and $R_2$ is hydrogen, and thereafter collecting serum from said host animal.

2. An antibody specific to methamphetamine prepared by inoculating a host animal with an immunogen of the formula

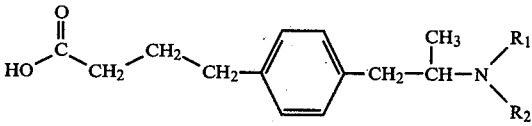

which is covalently bonded through the carboxyl group to an immunogenic carrier material, where $R_1$ is methyl and $R^2$ is hydrogen and thereafter collecting serum from said host animal.

3. The antibody of claim 1 or 2 wherein said immunogenic carrier material is bovine serum albumen.

* * * * *